US00PP36539P2

(12) United States Plant Patent
Koene

(10) Patent No.: US PP36,539 P2
(45) Date of Patent: Mar. 11, 2025

(54) MANDEVILLA PLANT NAMED 'Sunpa 423'

(50) Latin Name: *Mandevilla hybrida*
Varietal Denomination: Sunpa 423

(71) Applicant: Tim Koene, Maasland (NL)

(72) Inventor: Tim Koene, Maasland (NL)

(73) Assignee: SUNTORY FLOWERS LIMITED, Tokyo (JP)

( * ) Notice: Subject to any disclaimer, the term of this patent is extended or adjusted under 35 U.S.C. 154(b) by 19 days.

(21) Appl. No.: 18/420,557

(22) Filed: Jan. 23, 2024

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

(56) References Cited

FOREIGN PATENT DOCUMENTS

JP WO2024090462 A1 * 5/2024 ..... A01H 6/08

* cited by examiner

*Primary Examiner* — Karen M Redden
*Assistant Examiner* — Zachariah Allan Kay
(74) *Attorney, Agent, or Firm* — C. Anne Whealy

(57) ABSTRACT

A new and distinct cultivar of *Mandevilla* plant named 'Sunpa 423', characterized by its vining and climbing plant habit; vigorous growth habit; freely branching habit; freely flowering habit; long flowering period; double-type flowers that are deep red in color; and good garden performance.

2 Drawing Sheets

Figure 1:
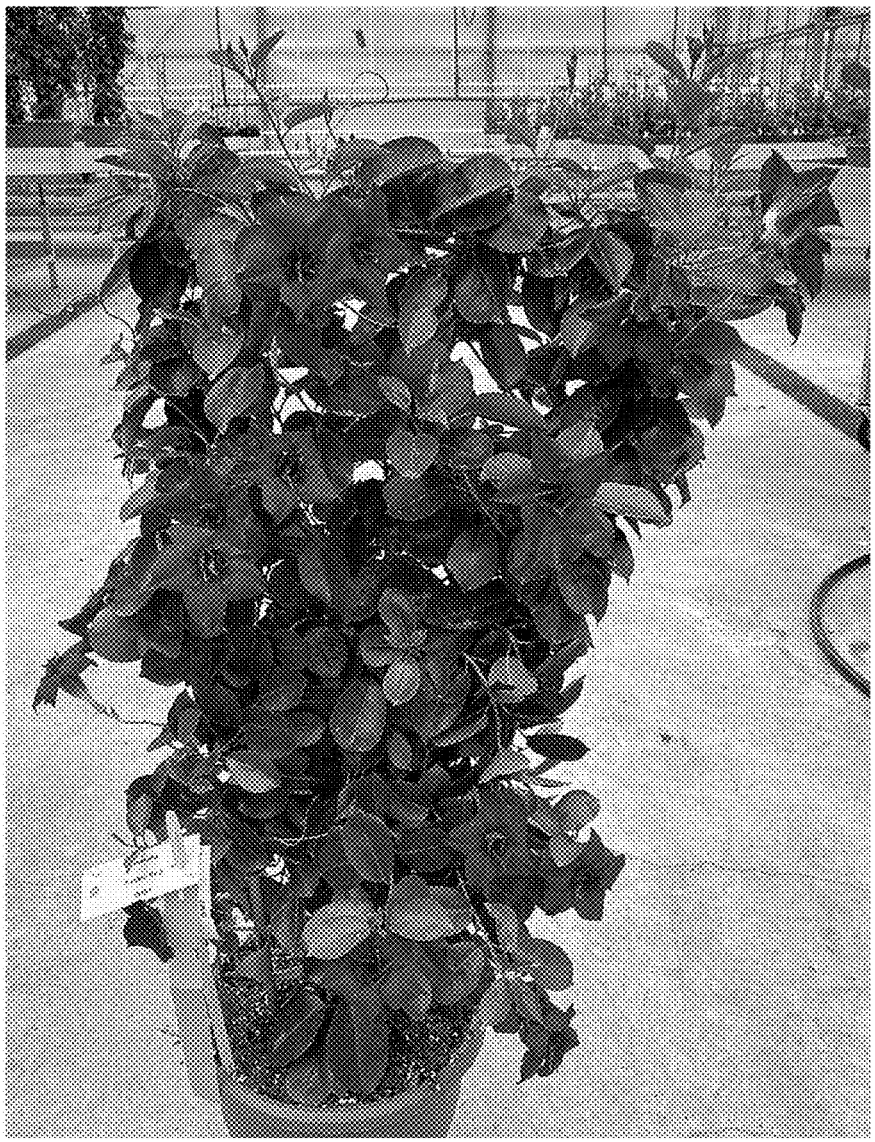

Botanical designation: *Mandevilla hybrida.*
Cultivar denomination: 'SUNPA 423'.

STATEMENT REGARDING PRIOR DISCLOSURES BY INVENTOR/APPLICANT and ASSIGNEE

An European Community Plant Breeder's Rights application for the instant plant was filed by the Assignee of the instant application, Suntory Flowers Limited of Tokyo, Japan on Jun. 28, 2022, application number 2022/1612. Foreign priority is not claimed to this application.

The Inventor/Applicant and Assignee assert that no sales, offers for sale or public distribution of the instant plant occurred more than one year prior to the effective filing date of this application.

Any information about the claimed plant would have been obtained from a direct or indirect disclosure from the Inventor/Applicant and/or Assignee. Inventor/Applicant and Assignee claim a prior art exception under 35 U.S.C. 102 (b)(1) for disclosures and/or sales prior to the filing date but less than one year prior to the effective filing date.

BACKGROUND OF THE INVENTION

The present invention relates to a new and distinct cultivar of *Mandevilla* plant, botanically known as *Mandevilla hybrida* and hereinafter referred to by the name 'Sunpa 423'.

The new *Mandevilla* plant is a naturally-occurring branch mutation of a proprietary selection of *Mandevilla hybrida* identified as code number Bp 20421, not patented. The new *Mandevilla* plant was discovered and selected by the Inventor on a single flowering plant from within a population of plants of the proprietary selection in a controlled greenhouse environment in Maasland, The Netherlands on Aug. 8, 2021.

Asexual reproduction of the new *Mandevilla* plant by terminal vegetative cuttings in Maasland, The Netherlands since Aug. 15, 2021 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 423'. These characteristics in combination distinguish 'Sunpa 423' as a new and distinct *Mandevilla* plant:

1. Vining and climbing plant habit.
2. Vigorous growth habit.
3. Freely branching habit.
4. Freely flowering habit.
5. Long flowering period.
6. Double-type flowers that are deep red in color.
7. Good garden performance.

Plants of the new *Mandevilla* can be compared to plants of the mutation parent selection. Plants of the new *Mandevilla* differ primarily from plants of the mutation parent selection in flower color as plants of the new *Mandevilla* have deep red-colored flowers whereas plants of the mutation parent have pink-colored flowers.

Plants of the new *Mandevilla* can be compared to plants of the *Mandevilla atroviolacea* X (*Mandevilla amabalis* x *boliviensis*) 'Sunmandecrim', disclosed in U.S. Plant Pat.

No. 15,539. In side-by-side comparisons, plants of the new *Mandevilla* differ from plants of 'Sunmandecrim' in the following characteristics:

1. Plants of the new *Mandevilla* have larger and darker green- colored leaves than plants of 'Sunmandecrim'.
2. Plants of the new *Mandevilla* flower later than plants of 'Sunmandecrim'.
3. Flowers of plants of the new *Mandevilla* are double-types whereas flowers of plants of 'Sunmandecrim' are single-types.
4. Flowers of plants of the new *Mandevilla* have larger sepals than flowers of plants of 'Sunmandecrim'.
5. Flower petals of plants of the new *Mandevilla* are imbricate whereas flower petals of plants of 'Sunmandecrim' are not imbricate.
6. Flowers of plants of the new *Mandevilla* do not produce seed whereas flowers of plants of 'Sunmandecrim' produce numerous seeds.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Sunpa 423' grown in a container.

Figure 2:
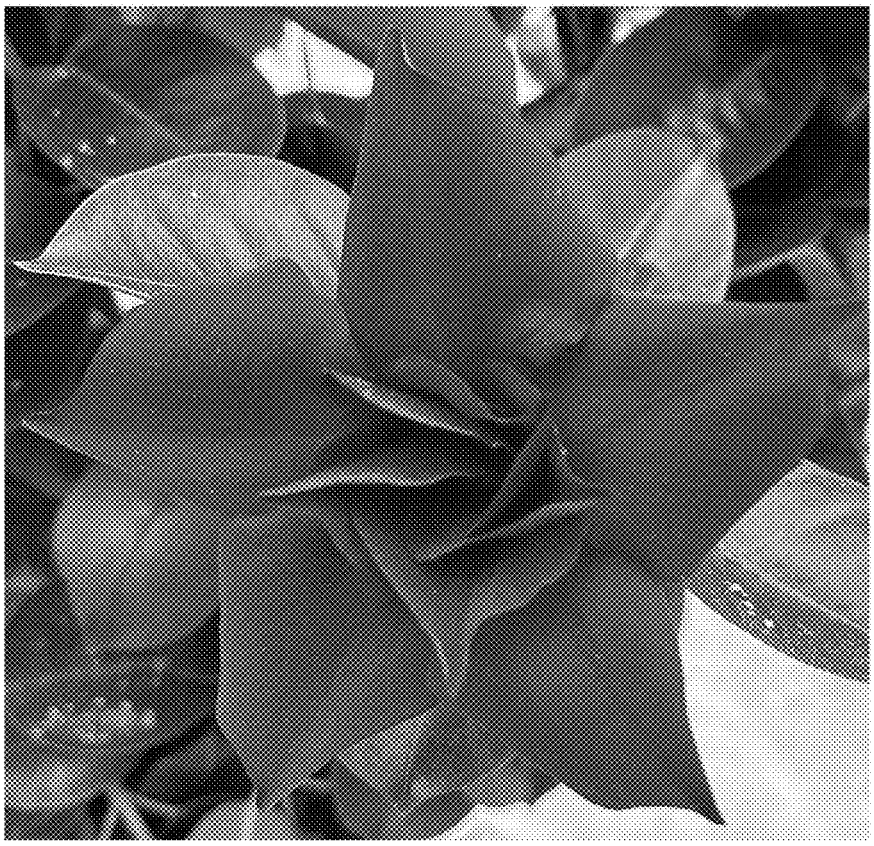

The photograph on the second sheet (FIG. 2) is a close-up view of a typical flower of 'Sunpa 423'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 423'.

Parentage: Naturally-occurring branch mutation of a proprietary selection of *Mandevilla hybrida* identified as code number Bp 20421, not patented.

Propagation:

*Type*.—By terminal vegetative cuttings.

*Time to initiate roots, summer and winter*.—About two weeks at temperatures about 23° C. to 25° C.

*Time to produce a rooted young plant, summer and winter*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Vining and climbing plant habit; vigorous growth habit; freely branching habit; suitable for hanging baskets and garden plantings.

*Lateral branch description*.—Length: About 190 cm. Diameter: About 2.7 mm. Internode length: About 6.9 cm. Strength: Strong, flexible. Texture: Smooth, glabrous. Color, developing: Close to 144A. Color, fully developed: Close to 152A.

Leaf description:

*Arrangement and quantity*.—Decussate, simple; medium density, about 22 per lateral branch.

*Length*.—About 6.3 cm.

*Width*.—About 4.2 cm.

*Shape*.—Ovate; incurving.

*Apex*.—Acuminate.

*Base*.—Cordate.

*Margin*.—Entire; not undulate to slightly undulate.

*Texture and luster, upper and lower surfaces*.—Smooth, glabrous; moderately glossy.

*Venation pattern*.—Pinnate, reticulate.

*Color*.—Developing leaves, upper surface: Close to 138A. Developing leaves, lower surface: Close to 145B. Fully expanded leaves, upper surface: Close to NN137A; venation, close to 143C. Fully expanded leaves, lower surface: Close to 137D; venation, close to 145A.

*Petioles*.—Length: About 1.3 cm. Diameter: About 1.7 mm. Texture, upper and lower surfaces: Smooth, glabrous. Color, upper and lower surfaces: Close to 143C.

Flower description:

*Flower type and habit*.—Double-type flowers; flowers face mostly outwardly; freely flowering habit with about three flowers per axil and typically about 18 flowers per plant.

*Natural flowering season*.—Late flowering habit, plants begin flowering about six weeks after planting rooted cuttings; long flowering period, plants flower continuously from summer until late autumn in Japan.

*Flower longevity on the plant*.—About seven to ten days; flowers not persistent.

*Fragrance*.—None detected.

*Flower buds*.—Height: About 5.9 cm. Diameter: About 1.4 cm. Shape: Rhombic. Color: Proximally, close to 145B and distally, close to 53A.

*Flowers*.—Appearance: Double-type, ten petals in two whorls; petals are imbricate. Diameter: About 8.1 cm. Depth (length): About 4.4 cm. Throat diameter, distally: About 1.9 cm. Throat diameter, proximally: About 9.6 mm. Throat length: About 3.1 cm. Tube length: About 1.4 cm. Tube diameter, proximally: About 5.6 mm.

*Corolla*.—Quantity and arrangement: Ten petals arranged in an outer whorl and a smaller inner whorl and fused towards the base into an elongated throat and tube; petal lobes imbricate. Petal lobe length: About 3.5 cm. Petal lobe width: About 3 cm. Petal lobe shape: Spatulate, strongly asymmetrical and convex. Petal lobe apex: Acute. Petal lobe margin: Entire; slightly undulate and slightly recurving. Petal lobe texture and luster, upper and lower surfaces: Smooth, glabrous; velvety; matte. Throat texture: Smooth, glabrous. Tube texture: Smooth, glabrous.

*Color*.—Petal lobe, when opening, upper surface: Close to 53A. Petal lobe, when opening, lower surface: Close to 53A and 63A. Petal lobe, fully opened, upper surface: Close to 60A; venation, similar to lamina colors; color does not change with subsequent development. Petal lobe, fully opened, lower surface: Close to 53A and 63A; venation, similar to lamina colors; color does not change with subsequent development. Throat, inner surface: Proximally, close to 170A and distally, close to 170A and 53A; venation, close to 171A. Throat, outer surface: Proximally, close to 63A and 150D and distally, close to 63A; venation, close 63A. Tube, inner surface: Close to 144C; venation, close to 144C. Tube, outer surface: Close to N34A and 144B; venation, close to N34A and 144B.

*Calyx*.—Quantity and arrangement: Five sepals arranged in a single whorl, fused at the base; calyx, star-shaped. Sepal length: About 7.7 mm. Sepal width: About 3.3 mm. Sepal shape: Lanceolate. Sepal apex: Acute. Sepal margin: Entire. Sepal texture, upper and lower surfaces: Smooth, glabrous. Sepal color, upper surface: Close to 138C; towards the apex, tinged with close to 63B. Sepal color, lower surface: Close to 138B; towards the apex, tinged with close to 63A.

*Peduncles*.—Length: About 1.9 cm. Diameter: About 2.4 mm. Texture: Smooth, glabrous. Aspect: Upright to outwardly. Color: Close to 138A.

*Pedicels*.—Length: About 1.5 cm. Diameter: About 2.5 mm. Texture: Smooth, glabrous. Aspect: Upright to outwardly. Color: Close to 138B.

*Reproductive organs*.—Stamens: Stamen development has not been observed, all stamens transformed into inner whorl of petals. Pistils: Quantity: Typically one. Pistil length: About 2.1 cm. Style color: Close to 145C. Stigma shape: Conical. Stigma color: Close to 145B. Ovary color: Close to 145A.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 423' as herein illustrated and described.

* * * * *